(12) United States Patent
Hirshberg

(10) Patent No.: US 9,149,073 B1
(45) Date of Patent: Oct. 6, 2015

(54) COMPRESSION SLEEVE FOR RETAINING ELECTRONIC DEVICES IN AN OPERABLE FORMAT WHILE AN INDIVIDUAL IS WEARING THE SLEEVE AND ENGAGING IN PHYSICAL ACTIVITIES

(75) Inventor: Jonathan Hirshberg, Manhattan Beach, CA (US)

(73) Assignee: JR286 Technologies, Inc., Torrance, CA (US)

( * ) Notice: Subject to any disclaimer, the term of this patent is extended or adjusted under 35 U.S.C. 154(b) by 479 days.

(21) Appl. No.: 13/484,771

(22) Filed: May 31, 2012

Related U.S. Application Data

(60) Provisional application No. 61/636,548, filed on Apr. 20, 2012.

(51) Int. Cl.
  *A45C 13/30* (2006.01)
  *A45F 3/14* (2006.01)
  *A41B 11/00* (2006.01)
  *A41B 5/00* (2006.01)

(52) U.S. Cl.
  CPC ............. *A41B 11/006* (2013.01); *A41B 5/00* (2013.01)

(58) Field of Classification Search
  CPC ...... A45F 2005/008; A41B 5/00; A41B 5/02; A41B 5/022; A41B 11/006
  USPC ............. 2/170; 206/320; 224/217, 218, 219, 224/222, 267, 270–272, 929, 930; 361/679.01–679.03, 679.55, 679.56, 361/807, 809; 455/575.1, 575.6, 575.8
  See application file for complete search history.

(56) References Cited

U.S. PATENT DOCUMENTS

| | | | |
|---|---|---|---|
| 4,746,043 A * | 5/1988 | Booker .................. 224/219 |
| 4,856,112 A | 8/1989 | Effle |
| 4,974,762 A * | 12/1990 | Boretsky et al. ............ 224/222 |
| 5,477,633 A * | 12/1995 | Leinberger ................ 2/16 |
| 6,092,235 A | 7/2000 | Santa Cruz |
| 6,321,957 B1 * | 11/2001 | Rossi .................. 224/221 |
| 6,330,961 B1 * | 12/2001 | Borja .................. 224/222 |
| D632,874 S | 2/2011 | Stephanis et al. |
| 8,099,794 B2 * | 1/2012 | Carstens ................ 2/16 |
| 2007/0170216 A1 * | 7/2007 | Davis .................. 224/222 |
| 2007/0194066 A1 * | 8/2007 | Ishihara et al. ........... 224/164 |
| 2007/0215663 A1 * | 9/2007 | Chongson et al. ........... 224/930 |
| 2008/0017678 A1 * | 1/2008 | Anderson et al. ........... 224/221 |
| 2009/0000002 A1 | 1/2009 | Hadash |
| 2009/0057357 A1 | 3/2009 | Rohrback et al. |
| 2010/0024088 A1 | 2/2010 | Griefer |
| 2010/0032462 A1 | 2/2010 | Cameron et al. |
| 2010/0319096 A1 | 12/2010 | Scott et al. |
| 2012/0042428 A1 | 2/2012 | Jarboe |
| 2013/0098955 A1 * | 4/2013 | Lamey et al. ............ 224/222 |
| 2014/0054335 A1 * | 2/2014 | Morgan et al. ............ 224/222 |

* cited by examiner

*Primary Examiner* — Luan K Bui
(74) *Attorney, Agent, or Firm* — Thomas I. Rozsa

(57) ABSTRACT

A mechanism within the garment for retaining an electronic device such as a smartphone or portable media player so that it can be in an in-use operational condition while an individual is wearing the garment and engaged in physical activity such as walking, running or other exercise. The mechanism is a compression sleeve which contains within it a pocket that extends through the body of the sleeve having a transparent window so that the electronic device can be inserted into the pocket and the screen of the electronic device can be viewed through the transparent window.

3 Claims, 12 Drawing Sheets

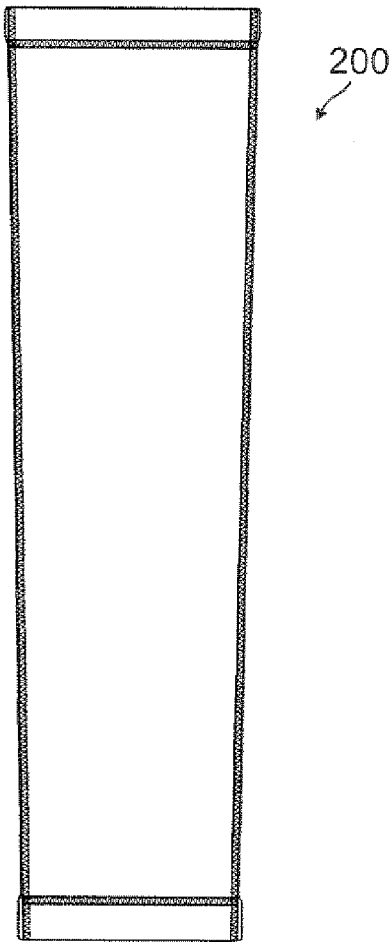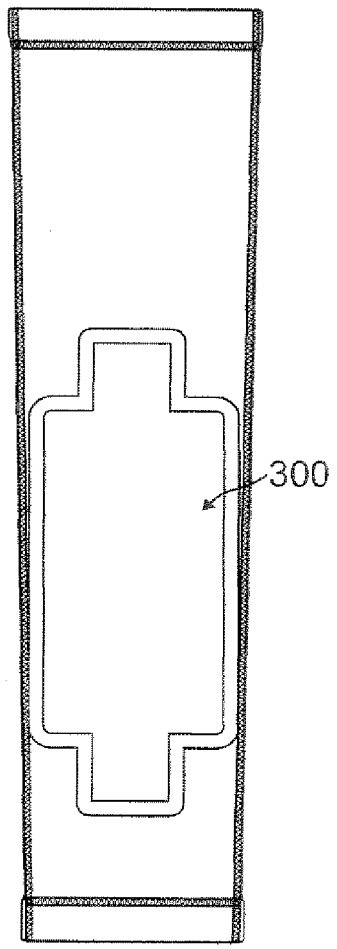
FIG. 3
FIG. 4

COMPRESSION SLEEVE FOR RETAINING ELECTRONIC DEVICES IN AN OPERABLE FORMAT WHILE AN INDIVIDUAL IS WEARING THE SLEEVE AND ENGAGING IN PHYSICAL ACTIVITIES

RELATED APPLICATIONS

This patent application claims priority to Patent Application Ser. No. 61/636,548 filed on Apr. 20, 2012.

BACKGROUND OF THE INVENTION

1. Field of the Invention

The present invention relates to the field of garments and also to the field of electronic devices and in particular, electronic devices such as a smart phone or portable media player, and for a mechanism within the garment for retaining the electronic device so that it can be in an in-use operational condition while an individual is wearing the garment and engaged in physical activity such as walking, running or other exercise.

2. Description of the Prior Art

Electronic devices such as smart phones, portable media players and other electronic devices are well known in the prior art. In most prior art, the electronic devices are retained in a pocket which is worn on a belt or is otherwise retained in a pouch which is worn on a belt or worn around a person's neck. These are both cumbersome and uncomfortable and it also makes it difficult to read the electronic device while engaged in an activity such as walking or running.

An information disclosure statement being filed concurrently with this application lists the prior art patents which are known to the inventor and are relevant to the field of the present invention.

There is a significant need for an improved apparatus to retain an electronic device on a garment in a manner in which the device is securely retained and is also in an operational condition wherein the device can be easily read or operated while the individual wearing the garment retaining the electronic device is engaged in a physical activity such as running, walking or other exercise.

SUMMARY OF THE INVENTION

The present invention is a compression sleeve which contains within it a pocket that extends through the body of the sleeve having a transparent window so that the electronic device can be inserted into the pocket and the screen of the electronic device can be viewed through the transparent window. The backing of the pocket contains an opaque material to act as a pouch to retain the electronic device such as a smart phone or portable media player.

The device is worn on a compression sleeve so that it is retained on the arm of an individual without the requirement of any additional affixation means. When the pocket for retaining the electronic device is located at the forearm, and the sleeve does not extend to the upper portion of the person's arm and only coves the forearm, then it is called a forearm shiver.

It is therefore an object of the present invention to provide a compression garment such as a compression arm sleeve or forearm shiver which contains a pocket extending through the garment to retain an electronic device with a transparent window so that the electronic device can be seen and operated while being worn on the forearm and while the individual is engaged in other activities such as walking, running etc.

It is a further object of the present invention to incorporate into the compression sleeve slots for retaining wires that extend from the electronic device to earphones, plugs or headphone plugs so that an individual can listen to the device while running and walking.

Further novel features and other objects of the present invention will become apparent from the following detailed description and discussion.

BRIEF DESCRIPTION OF THE DRAWINGS

Referring particularly to the drawings for the purpose of illustration only and not limitation, there is illustrated:

FIG. 3 is rear elevational view showing the outside of the arm of the compression sleeve;

FIG. 4 is a view of the interior of the sleeve showing the interior pocket which retains the electronic device;

FIG. 9A is an inside arm view without hood layer, also known as a forearm shiver also containing the transparent plastic sleeve for retaining the electronic device of the present invention in the forearm portion of the shiver;

FIG. 12A is an enlarged view of the headphone-earbud cord window;

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

Figure 1:
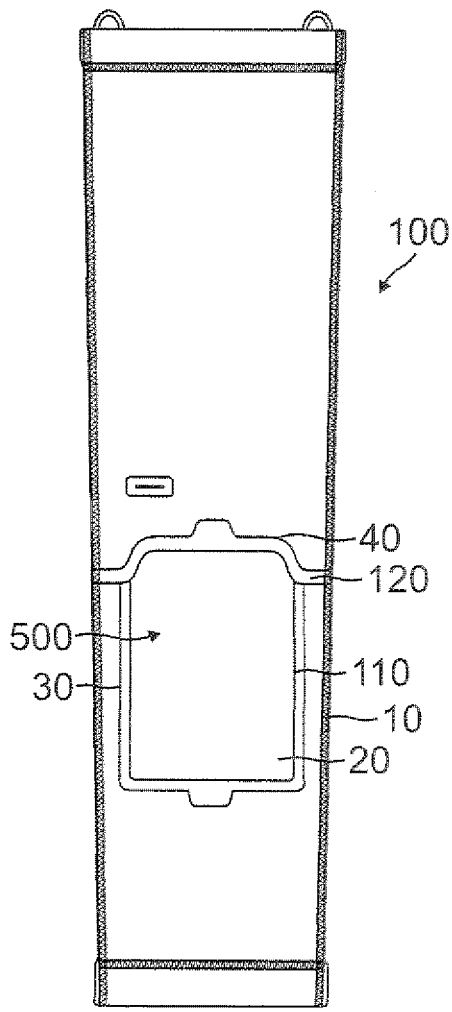
FIG. 1 is a side elevational view of the inside of the arm of the compression sleeve with a hood layer illustrating the present invention apparatus for retaining an electronic device in the interior forearm portion of the sleeve.

Referring to FIG. 1, there is illustrated an inside view of the exterior of an arm of the compression sleeve with a hood layer 100. The device consists of a garment made of fabric compression material such as neoprene. An opening 120 is cut within the garment which extends through the entire thickness of one side of the sleeve 110. On the exterior 10 of the garment is a clear plastic sleeve 20 which is affixed to the garment by adhesive means such as thermoplastic polyurethane (hereafter "TPU") 30. The sleeve is entirely affixed around the bottom and on both sides and partially affixed on the top with an opening flap 40 so that the electronic device 500 can be retained and inserted into the location where the sleeve is found.

Figure 2:
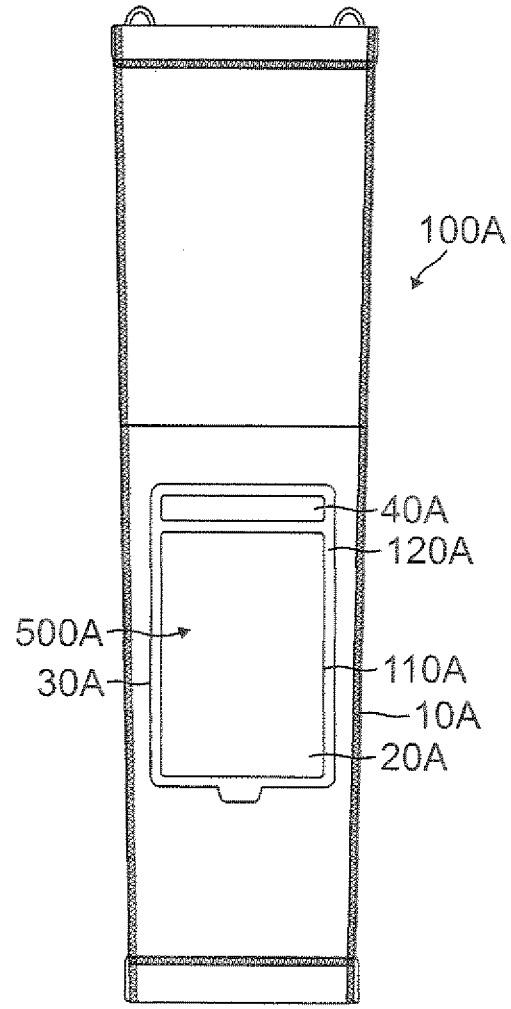
FIG. 2 is a side elevational view of the inside of the of the compression sleeve with a transparent view of the hood layer illustrating the present invention apparatus for retaining an electronic device in the interior forearm portion of the sleeve.

Referring to FIG. 2, there is illustrated an inside view of the exterior of an arm of a compression sleeve with a hood layer 100A. The device consists of garment made of fabric compression material such as neoprene. An opening 120A is cut within the garment which extends through the entire thickness of one side 110A of the sleeve. The exterior 10A of the garment is an opaque sleeve 20A which is affixed to the garment by adhesive means 30A such as TPU. The sleeve is entirely affixed around the bottom and on both sides and partially affixed on the top with an open flap 40A so that the electronic device 500A can be inserted into the location of the sleeve. Preferably, the opening is on the inside of the forearm so that the outside of the arm which is depicted in FIGS. 3 and 4 is opaque and therefore, the device itself will not be damaged by accidentally being hit against an object while an individual is engaged in physical activity.

Referring to FIG. 3, the outside of the compression sleeve arm 200 is solid and does not contain any material other than neoprene and serves as a protective barrier so that the electronic device 500 will not hit against any object as a user is walking or running.

Figure 5:
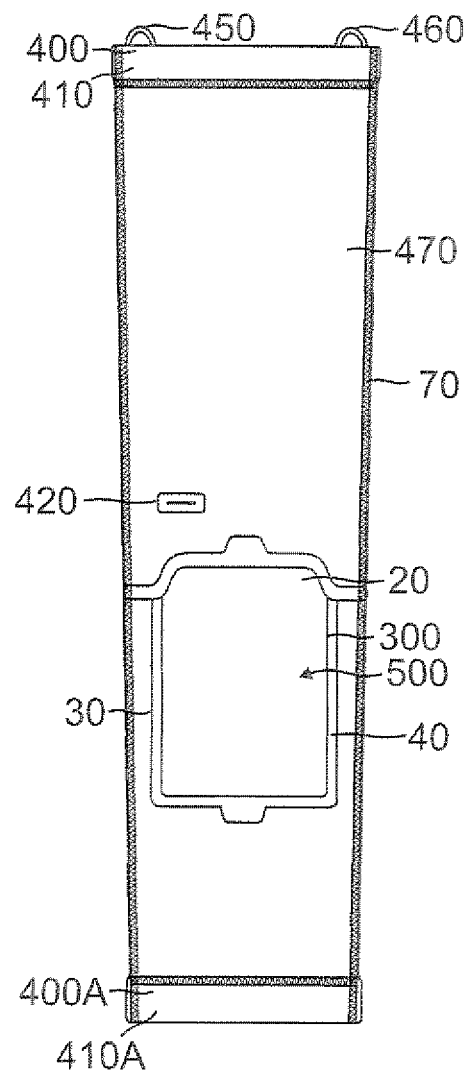
FIG. 5 is an interior side view of the arm with the hood layer illustrating the present invention apparatus for retaining an electronic device on the interior portion of the compression sleeve, the arm containing a hood layer.
Figure 6:
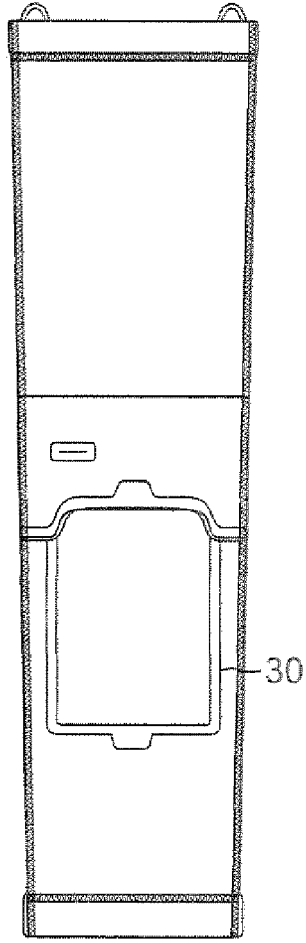
FIG. 6 is an inside transparent view of the hood layer also showing the interior of the compression sleeve with the present invention device for retaining an electronic device within the interior of the compression sleeve.
Figure 7:
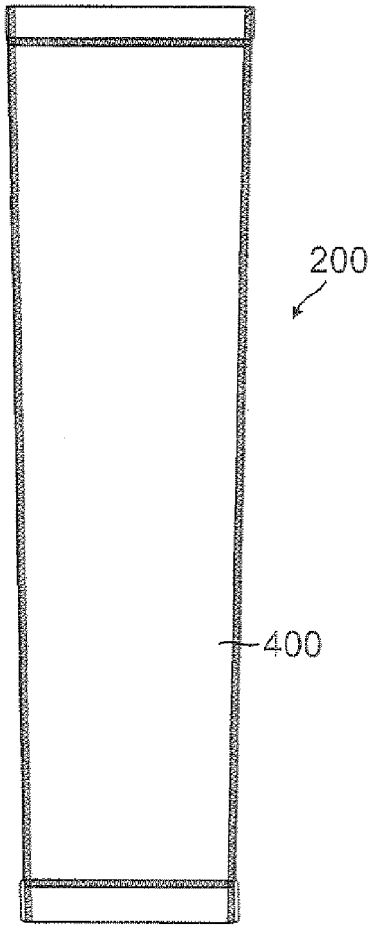
FIG. 7 is an outside view of the outside of the arm of the compression sleeve.

Referring to FIG. 4, there is shown the inside of the sleeve which reveals the pocket 300 which is designed to retain the electronic device. A clearer view of the device is shown in FIG. 5. FIG. 5 is an inside view of the arm with the hood layer. FIG. 6 is an inside arm view with a transparent view of the hood layer. It is basically the same interior view with the hood layer being transparent in FIG. 6.

Referring to FIG. 5, there is illustrated the inside of the sleeve 470 which contains a pocket 300 which is affixed to the inside of the sleeve by adhesive material 30 such as TPU. The pocket 300 is in communication with the exterior sleeve transparent cover 20 so that the electronic device 500 can be inserted behind the exterior sleeve transparent cover 20 and viewed from the inside of the forearm while the electronic device itself is retained in the pocket 300 which is securely adhered to the interior forearm sleeve of the garment by TPU or other very strong adhesive means.

Figure 8:
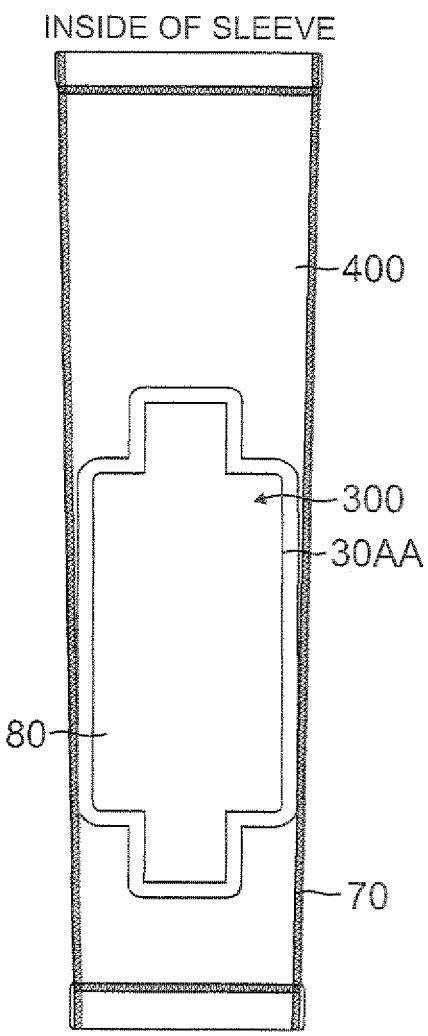
FIG. 8 is an inside view of the compression sleeve showing the pocket for retaining the electronic device which is immediately behind the transparent window from which the electronic device can be seen.

Referring to FIGS. 5 and 8, there is illustrated the inside of the sleeve which contains material of the dri-fit fabric 400 and heavy stitching 70 along the outside. The pocket 300 is affixed to the sleeve 400 by strong adhesive such as TPU 30AA which in turn contains an opaque material 80 which forms the rear portion of the pocket on the inside of the sleeve 100, the material of the pocket being made by way of example of 87% polyester and 13% spandex. It is the pocket 300 that retains the electronic device 500 which can be viewed through the transparent window 20.

In addition, illustrated in FIG. 5 there is illustrated the fabric material dri-fit 400 and the 2 cm. of elastic 410. Comparable material 400A and 410A is shown at the bottom of the sleeve. In addition to that, the inside of the sleeve arm 470 is made of black matte material and there are also shown loops 450 and 460 to retain the cord that comes from the electronic device and is connected to the ear jack which the person is wearing.

Figure 9:
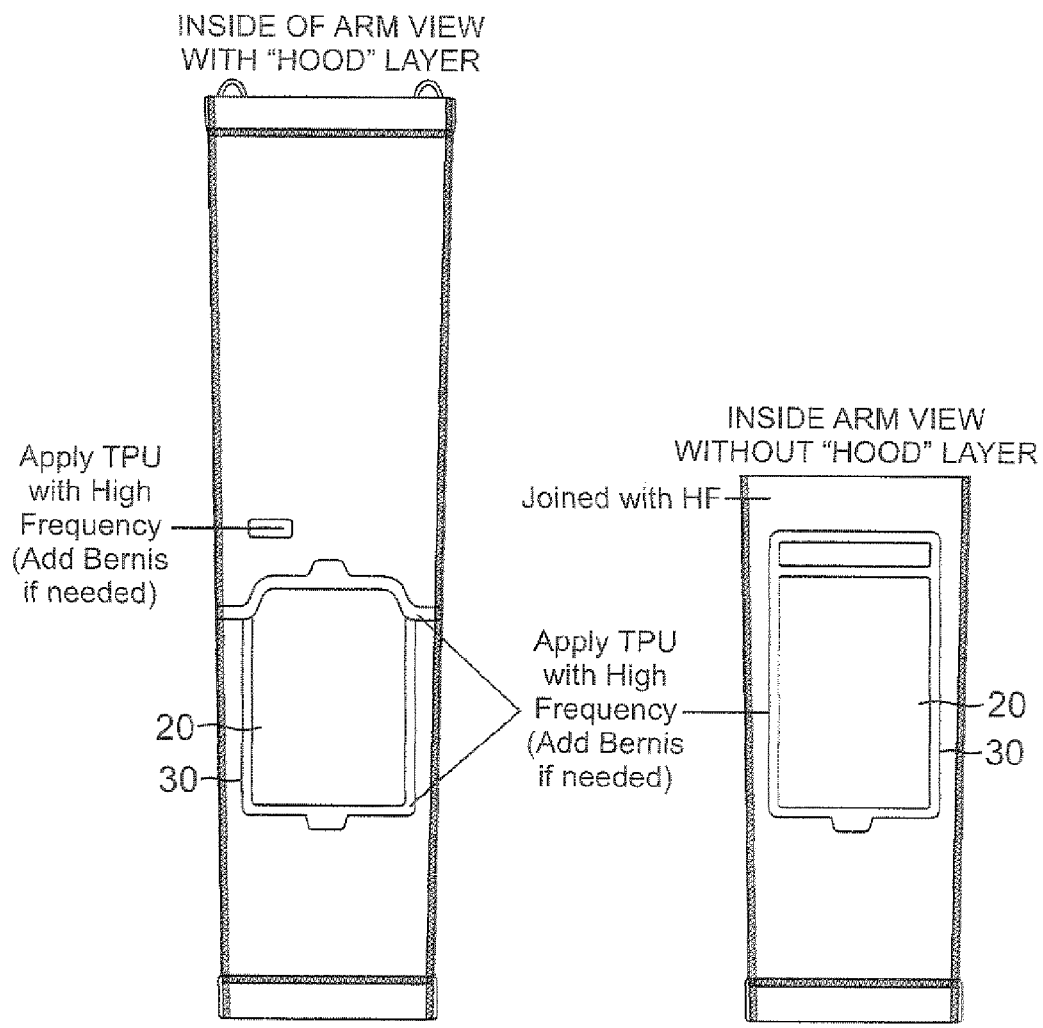
FIG. 9 is an inside view of the arm with a hood layer showing the present invention device for retaining an electronic device on the interior of the sleeve.

Referring to FIG. 9, the entire compression sleeve is known as a compression sleeve with a hood layer. Where only the lower portion of the forearm as in FIG. 9A is used and the upper portion of the arm is not used, the device is known as a forearm shiver. Either way, it operates in the same manner in that there is a clear window 20 which is affixed to the forearm shiver by strong adhesive such as TPU 30 and behind it is a pocket of opaque material 80 (see FIG. 8) affixed to the interior of the sleeve 100 to retain the electronic device 500 in a secure manner; whereas the entire outside of the sleeve 200 does not have any device to be covered by a protective cushioning so that the electronic device would not be hit against an object while an individual is engaged in fast walking and running.

Figure 10:
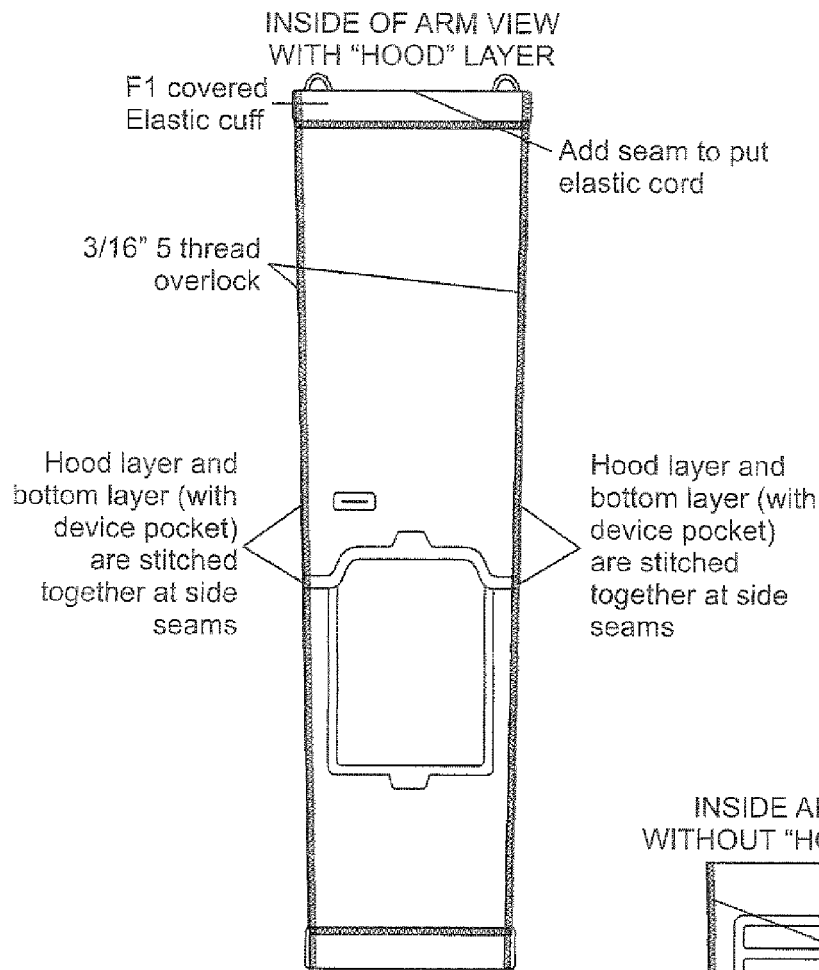
FIG. 10 is a view of the inside of the arm with the hood layer for a full compression sleeve showing the transparent pocket for retaining the electronic device.

Referring to FIG. 10, there is described in words the inside of the arm view with the hood layer showing the elastic cuff and the added seam to retain the elastic cord. There is also a 3/16th 5" thread overstock material and the hood layer and bottom layer (with pocket device) are stitched together at the side seams and the hood layer and bottom layer stitched together at the side seams on either side.

Figure 11:
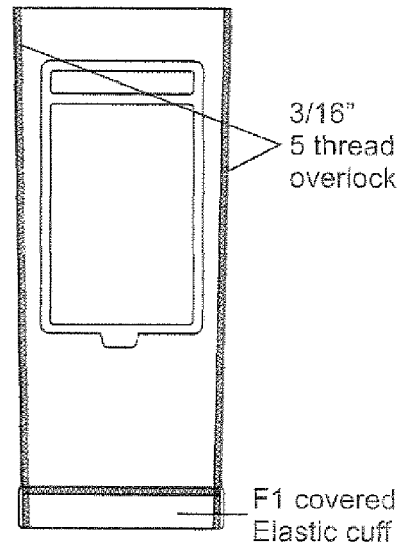
FIG. 11 is an inside arm view without the hood layer showing the forearm shiver also illustrating the transparent window through which the electronic device can be viewed.

Referring to FIG. 11 again using only words, there is disclosed the inside arm without a hood which discloses the 3/16th 5" thread overstock material for the pocket and an elastic covered cuff.

Figure 12:
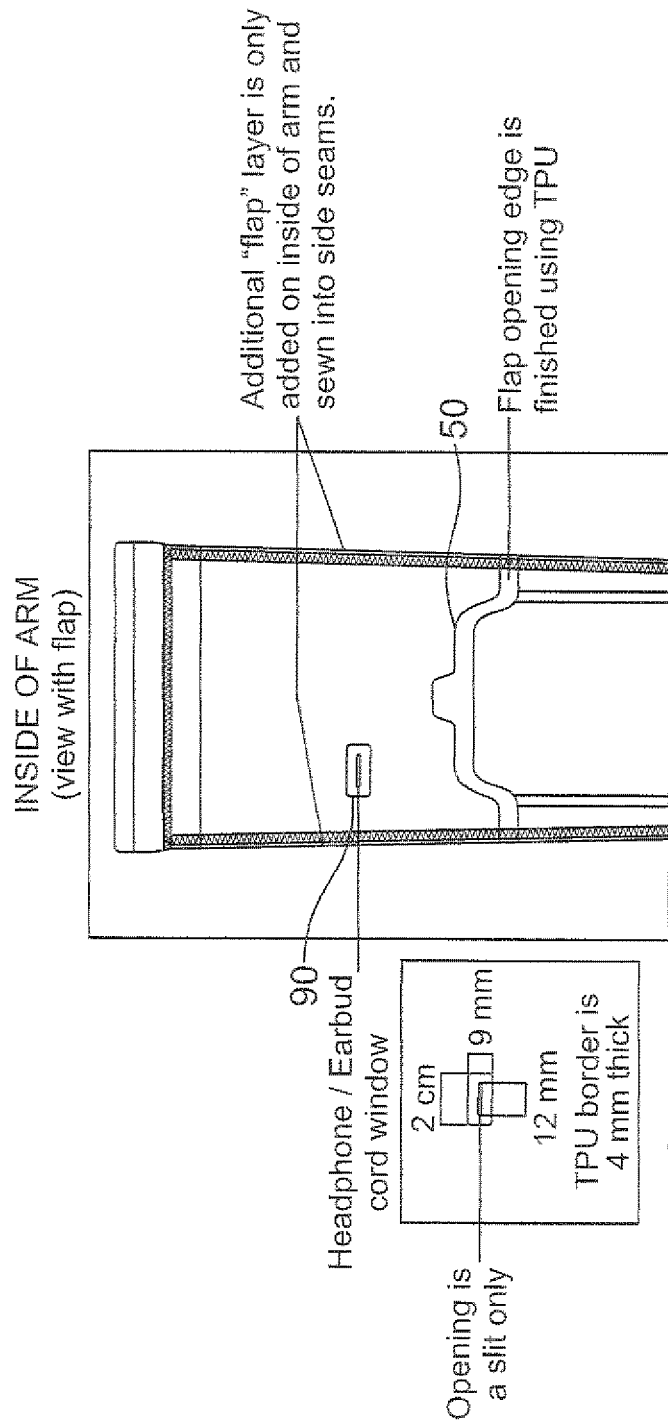
FIG. 12 is an inside view of the arm with the flap for opening the arm and enabling the electronic device to be inserted between the pocket and the transparent window, also illustrating the headphone earbud cord window through which an electronic cord is extended from the electronic device to a headphone listening device.
Figure 13:
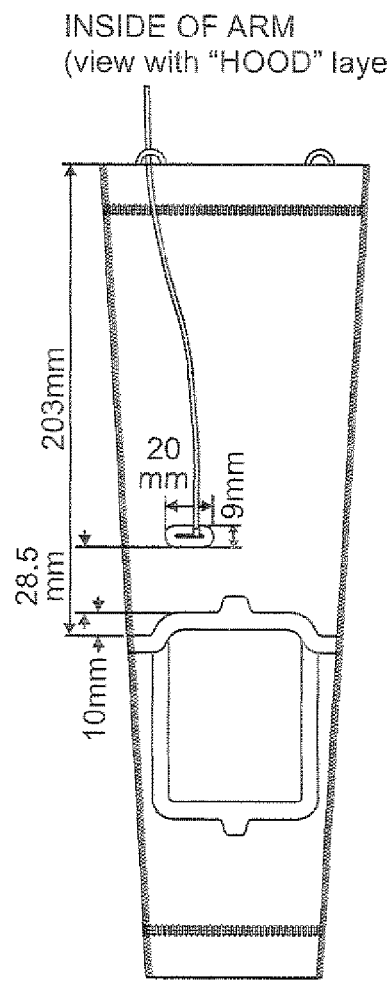
FIG. 13 is an inside view of the arm with a view of the hood also illustrating the electronic cord connecting the electronic device to an ear plug.
Figure 14:
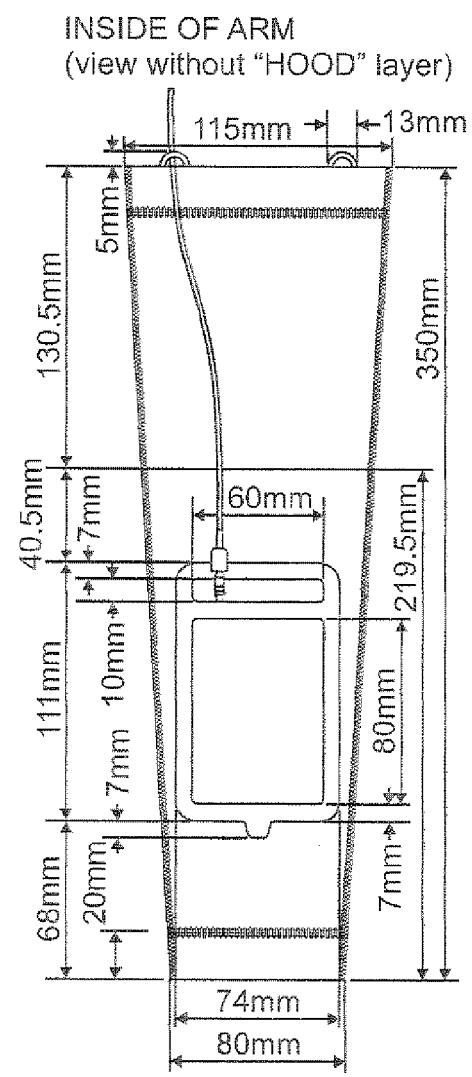
FIG. 14 is an inside view of the arm with a view of the hood layer also illustrating the electronic cord connecting the electronic device to an ear plug with dimensions shown.

FIG. 12 is a view of the inside of the arm with a view of the flap 50 which is folded over in order to be able to insert the electronic device 500 into the pocket 80. On either side of the sleeve there is an additional flap layer that is only added on the inside of the arm and sewn into side seams. The flap opening edge is finished using TPU and is illustrated so that the flap edge 50 can open so that the pocket 300 is accessible so that the electronic device 500 can be inserted into the pocket 300 and viewed through the transparent screen 20. Also shown is the headphone ear bud cord window 90 which is a slit (shown in greater detail in the exploded view of FIG. 12A) so that the cords depicted in FIG. 13 and FIG. 14 can be extended from the electronic device to head phones that an individual would be wearing. By way of example, certain dimensions are shown in FIGS. 13 and 14. Also, with respect to FIG. 15, the back pocket is also shown with dimension lines showing one preferred embodiment for the size dimensions for the pocket.

FIG. 13 shows the inside of the arm viewed with a hood layer and FIG. 14 shows an inside of an arm viewed without a hood layer.

Figure 15:
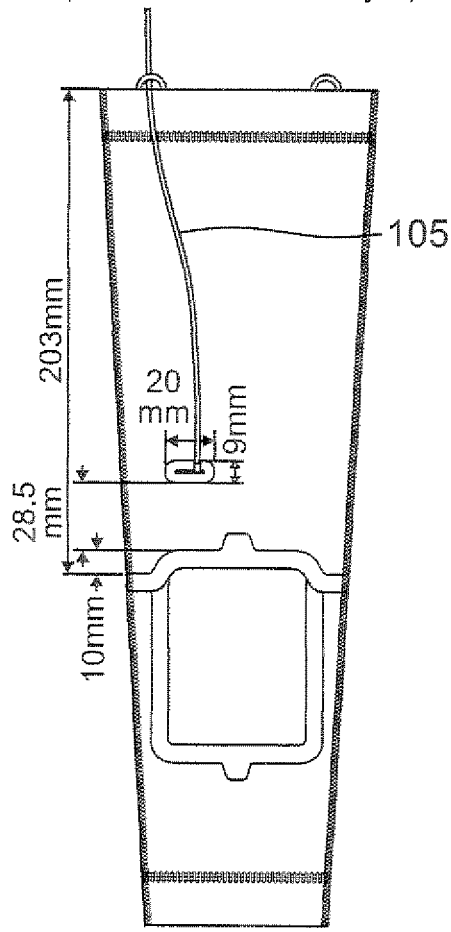
FIG. 15 is an inside view of the arm with the hood layer illustrating certain dimensions and illustrating the electronic cord which extends from the electronic device to an ear plug.
Figure 16:
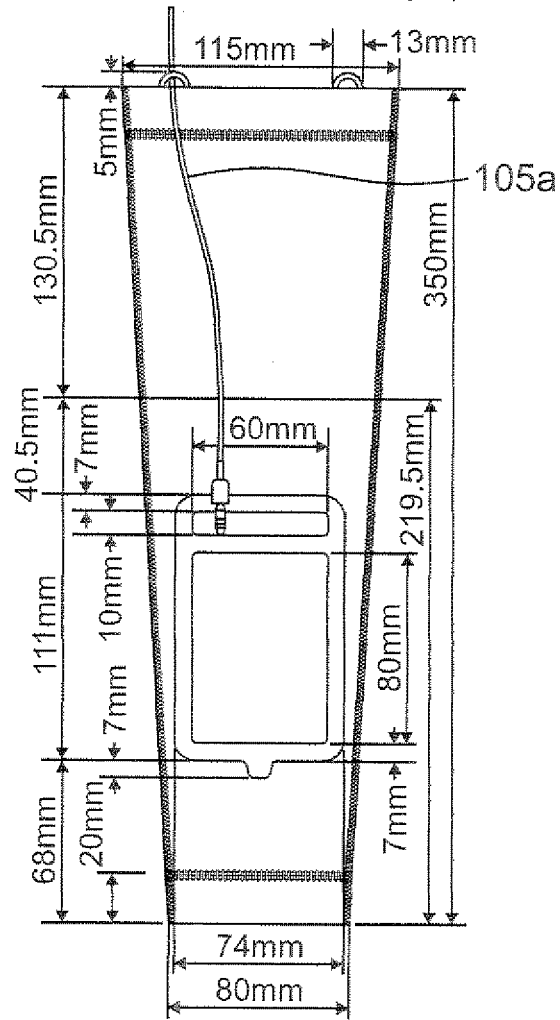
FIG. 16 is an inside view of the arm with the hood layer illustrating certain dimensions and illustrating the electronic cord which extends from the electronic device to an ear plug with dimensions shown.

In an alternative variation shown in FIG. 15 and FIG. 16, FIG. 15 shows the inside of the arm viewed with the hood layer including the electronic cord 105 that goes from the electronic device to ear plugs. 105A for the comparable cord is shown in FIG. 16.

Figure 17:
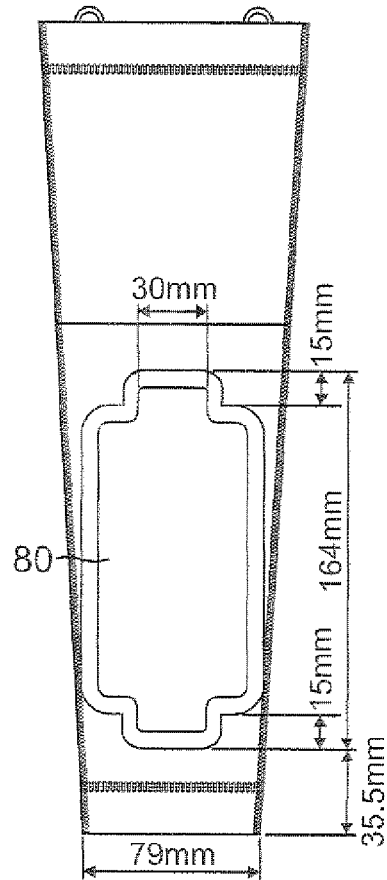
FIG. 17 is an inside view of the sleeve illustrating the pocket for retaining the electronic device on the interior inside portion of the sleeve in line with the transparent window viewable from the outside of the portion of the interior sleeve.
Figure 18:
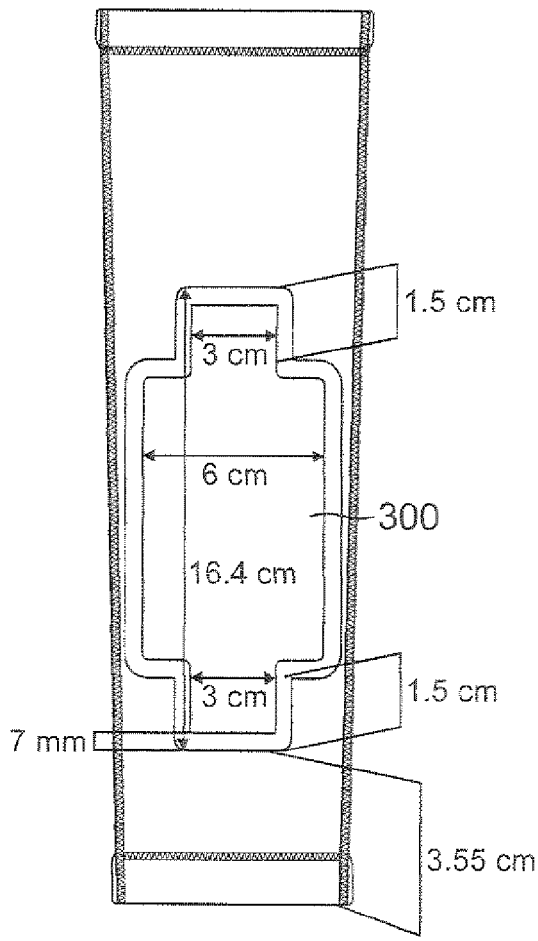
FIG. 18 is a cross-sectional interior view of the inside of the sleeve showing the pocket for retaining the electronic device.

FIGS. 17 and 18 show an interior view of a sleeve with certain dimensions for the pocket 300 being illustrated as one representative example of a pocket sized to fit an electronic device such as smart phone.

Figure 19:
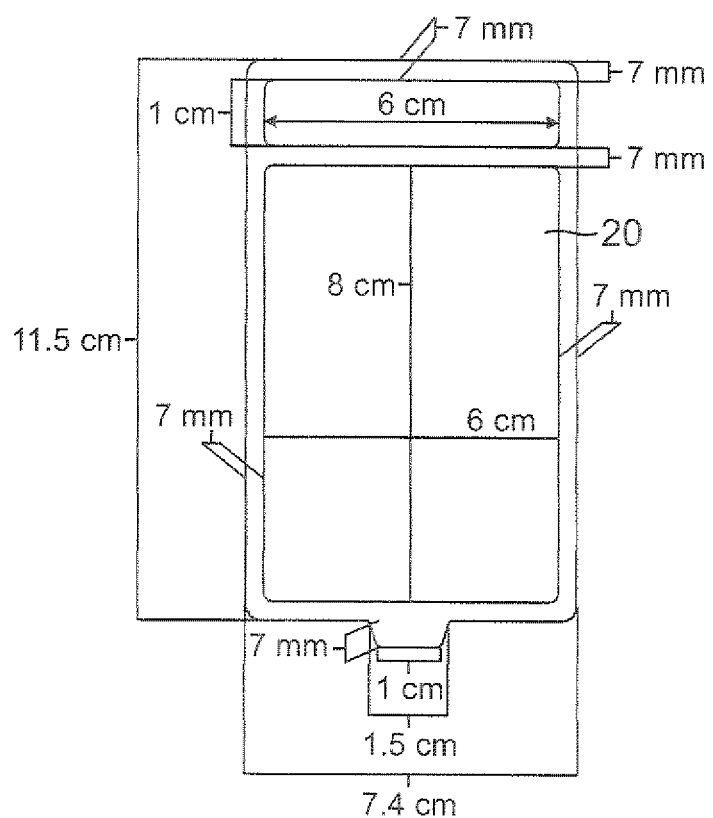
FIG. 19 is an outside view of the pocket and transparent view for viewing the electronic device.

FIG. 19 is an outside view of the sleeve showing the clear plastic window 20 in various dimensions which can accommodate an electronic device retained by the present invention.

For the preferred embodiment, the compression sleeve 100 is made out of material such as dri-fit fabric 400 which is 88% polyester and 12% spandex. The plastic sheet 20 which is affixed to the dri-fit fabric can be any type of sanded plastic sheet. Immediately below this level is a 2 cm. elastic 410 so that the compression sleeve is tightly fit around the upper arm. Also incorporated into the body of the sleeve is a TPU and BemisTape headphone cord holder 420. The border 40 for the plastic sheet 20 through which the electronic device 500 can be seen is made of TPU and BemisTape. On the bottom of the sleeve located adjacent the wrist there is located a second dri-fit fabric 400A and immediately below that, 2 cm. of elastic 410A.

In the variation which contains an inside of an arm with a hood layer, there are located a pair of spaced apart elastic loops 450 and 460 which can be 1.5 mm. thick so that the cord from the electronic device which leads to ear plugs can extend through the loop.

On the outside of the arm 200, the outside material is also made of dri-fit fabric 400 so that it will not scratch and the electronic device is not located on the outside of the arm so it cannot accidentally be hit against any object as an individual is engaged in physical activity such as fast walking or running. With respect to the inside of the sleeve which contains the pocket 300, the entire exterior surface of the sleeve is stitched with heavy stitching 70 to make sure that the compressions sleeve is securely fit around the individual's arm and will not fall off while the individual is engaged in vigorous exercise such as fast walking and running and at the same time retaining the electronic device in the present invention sleeve pocket where it can be viewed through the transparent window 20 and is securely retained within the pocket 300.

In summary, the present invention is a compression sleeve which can either contain a hood so that the sleeve extends all the way up from the forearm through the upper arm or is simply a forearm shiver which only extends around the forearm and contains on the interior portion of the sleeve an opening with a transparent sheet that is affixed to the material of the shiver or compression sleeve with a strong adhesive such as TPU and immediately behind it and in continuous relationship with it is a pocket 300 that is made of opaque material and is affixed by TPU or other strong adhesive material to the interior portion of the spandex sleeve which is hidden from view from the outside and has the pocket to retain the electronic device 500. On the opposite side of the compression sleeve is a flat surface which contains no material and which serves as a buffer so that in the event a person hits their arm against an object, it shields the electronic device which is on the interior of the sleeve from being hit against the object and prevents it from being damaged.

In the preferred embodiment, the compression sleeve is sold in pairs so that the user can have two separate electronic devices, retained on the compression sleeve forearm portion of each separate compression sleeve.

In the preferred embodiment, the entire sleeve 100 and 200 is made of 88 percent polyester and 12 percent spandex. The pocket 300 is made of 87 percent polyester and 13 percent spandex Insofar as the description above and the accompanying drawings disclose any additional subject matter that is not within the scope of the claims below, the inventions are not dedicated to the public and the right to the one or more applications to claim such additional inventions is reserved.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. An apparatus for use in conjunction with an entire length of a human arm, and also used in conjunction with a portable electronic device, the apparatus comprising;
   a. a compression sleeve having an exterior and an interior with a given thickness between the exterior and the interior, an opening on the exterior of the compression sleeve, the opening extending into the thickness of the compression sleeve, a clear plastic sleeve affixed onto the exterior of the compression sleeve and aligned with the opening in the compression sleeve, the clear plastic sleeve having a bottom side affixed onto the exterior of the compression sleeve, a pair of opposite sides affixed onto the exterior of the compression sleeve and a top with an opening;
   b. a pocket formed within the compression sleeve and aligned with the opening in the compression sleeve, the pocket having an interior opening through which a portable electronic device is inserted into the pocket and viewed through the clear plastic sleeve;
   c. the compression sleeve made of dry-fit fabric which includes 88% polyester and 12% spandex, the clear plastic sleeve affixed to the dry-fit fabric, a layer of elastic at a location on the compression sleeve and separated from the clear plastic sleeve, the compression sleeve including an additional section adjacent the layer of elastic, the additional section made of dry-fit fabric and further including an additional adjacent layer of elastic material;
   d. the compression sleeve including openings through which wires from headphones connected to the portable electronic device retained within the pocket can be inserted in an operable condition; and
   e. a hood section incorporated into the compression sleeve, the hood section enabling the apparatus to be retained on an arm of a human body from a wrist to an underarm of the body, and securing the apparatus to the arm so that the portable electronic device will not inadvertently fall our of the pocket during vigorous exercise of the body.

2. The apparatus in accordance with claim 1, further comprising:
- the clear plastic sleeve has a foldover pocket to retain the object between the clear plastic sleeve and the pocket.

3. The apparatus in accordance with claim 1, further comprising:
- the pocket has a foldover flap to retain an object within the pocket.

\* \* \* \* \*